United States Patent [19]

Ross

[11] 4,017,734
[45] Apr. 12, 1977

[54] WATER PURIFICATION SYSTEM UTILIZING ULTRAVIOLET RADIATION

[76] Inventor: Henry M. Ross, The Lawn, Nokesville, Va. 22123

[22] Filed: Mar. 24, 1976

[21] Appl. No.: 669,767

Related U.S. Application Data

[63] Continuation-in-part of Ser. No. 509,871, Sept. 27, 1974, abandoned.

[52] U.S. Cl. .................................. 250/431; 250/435
[51] Int. Cl. ........................................... G01n 21/24
[58] Field of Search .................... 250/431–438, 250/301, 372, 373

[56] References Cited
UNITED STATES PATENTS

| | | |
|---|---|---|
| 3,061,721 | 10/1962 | Brenner .......................... 250/431 |
| 3,182,191 | 5/1965 | McFarland et al. ................ 250/435 |
| 3,182,193 | 5/1965 | Ellner et al. ........................ 250/431 |
| 3,456,107 | 7/1969 | Robertson .......................... 250/431 |

*Primary Examiner*—Davis L. Willis

[57] ABSTRACT

A water purification system utilizes an ultraviolet generator encased in a quartz cylinder to irradiate water flowing through a passageway defined by the surface of the quartz cylinder and an outer casing. An ultraviolet sensor and control circuit shuts off the water when the ultraviolet radiation level drops below a predetermined level. A flow-sensing switch controls an ultraviolet dimming circuit which reduces the generator output when water is not flowing. Water flow is controlled by reduced annular spaces at the inlet and outlet of the passageway and the quartz cylinder and the ultraviolet sensor are kept free of sedimentation by wiper blades.

7 Claims, 3 Drawing Figures

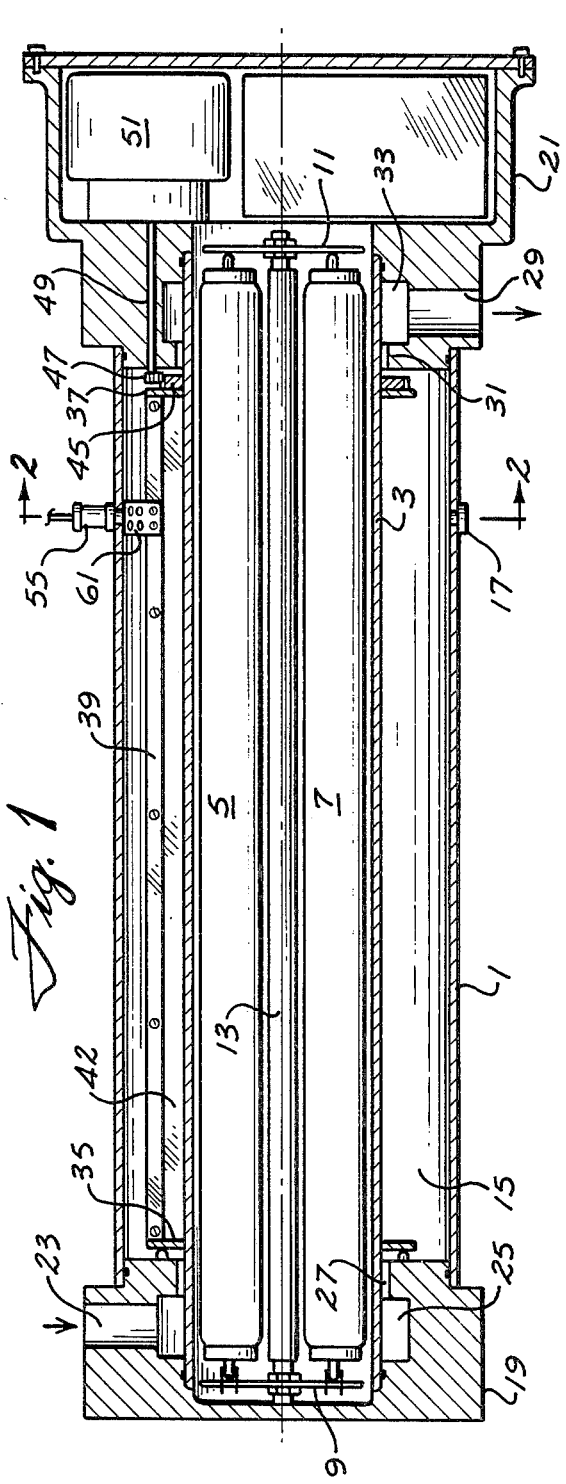
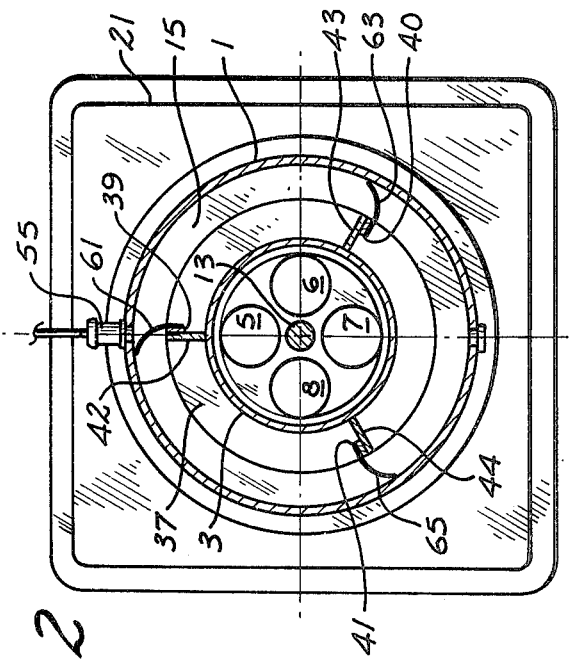
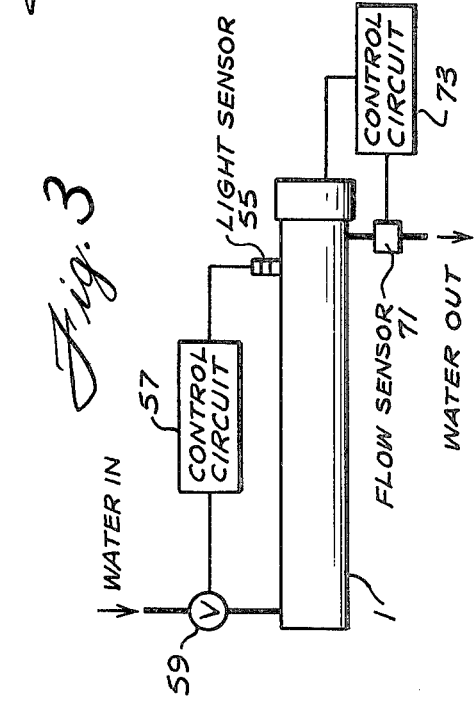

WATER PURIFICATION SYSTEM UTILIZING ULTRAVIOLET RADIATION

CROSS-REFERENCE TO RELATED APPLICATIONS

This application is a continuation-in-part of Ser. No. 509,871, filed Sept. 27, 1974 and now abandoned by Henry M. Ross for "Water Purification System Utilizing Ultraviolet Radiation".

BACKGROUND OF THE INVENTION

The invention relates to water purification equipment which is designed to kill all germs and microorganisms contained in water without the use of chemicals and without affecting the taste or odor of the water.

One of the most important considerations in selecting a habitation is the availability of a potable water supply. In the past impure sources of water have been treated with chemicals to render harmless the dangerous organisms. Such treatment is effective in removing the danger of disease to humans but a new problem is then created because of the residual chemical taste and odor which are unacceptable to many people. It would be highly desirable to be able to purify the water without imparting a chemical taste or odor.

SUMMARY OF THE INVENTION

The present invention accomplishes the desired objective of purification without addition of taste or odor by employing ultraviolet radiation as a sterilization medium. The water is caused to flow through an annular passageway surrounding an ultraviolet generator protected by a quartz cylinder. A flow sensing switch operates an ultraviolet dimming circuit to reduce the generator output when water is not flowing, thereby conserving energy and increasing generator life. An ultraviolet sensor shuts off water fow in the event that the ultraviolet radiation level drops below a predetermined level. The flow is limited by constrictions in the passageway and the optical efficiency of the quartz cylinder and the ultraviolet sensor are maintained by motor driven stainless steel wiper blades which continually remove any surface sediment deposits.

The unit embodying the features of the invention comprises an outer steel case concentrically surrounding a quartz cylinder which encloses a plurality of ultraviolet tubes. Annular rings at either end of the quartz cylinder have a plurality of wiper blades extending therebetween to ride on the surface of the quartz cylinder. The wiper blade assembly is driven by a motor through connecting gearing. A monitoring peep hole with protective optical filtering is provided in the outer case to observe the interior operation.

An ultraviolet sensor is mounted in the outer case and connected to a control circut which operates a water inlet valve. Separate wiper blades connected to the wiper blade assembly are provided for the ultraviolet sensor to remove foreign deposits. A flow-sensing switch at the outlet end controls an ultraviolet dimming circuit so that the ultraviolet generator runs at full output only when water is flowing through the unit.

BRIEF DESCRIPTION OF THE DRAWING

FIG. 1 is a cross-sectional view of a unit constructed in accordance with the features of the invention;

FIG. 2 is a section taken along line 2—2 of FIG. 1; and

FIG. 3 is a diagrammatic representation of the system.

DESCRIPTION OF THE PREFERRED EMBODIMENT

The invention will be understood by referring to the drawing in which the cross-sectional view of FIG. 1 shows an outer steel tubular member 1 having an inner quartz cylinder 3 mounted concentrically therein. Positioned within the quartz cylinder 3 are four ultraviolet tubes 5-8 mounted between end plates 9 and 11 which are held in spaced relationship by rod 13. An annular passageway 15 is formed between tubular member 1 and quartz cylinder 3. A peephole 17 equipped with an appropriate optical filter to prevent eye damage is positioned in tubular member 1 to permit viaual monitoring of the internal parts during operation.

An ultraviolet sensor 55 is provided to monitor the ultraviolet radiation level within the tubular member 1 and provide a signal to control circuit 57 to shut off valve 59 and stop the water flow in the event that the radiation level drops below a predetermined level. The sensor 55 consists of a filter, a phosphor, and a photoconductive cell. The filter serves to block visible light from passing through the filter to the phosphor, but allows ultraviolet light of wavelength 253.7 nanometers to pass through. This is the primary wavelength of the "killing" ultraviolet produced by the ultraviolet generators within the unit. The phosphor, zinc silicate, is excited by the ultraviolet photons and emits visible green light of wavelength 520 nanometers. This visible light is "seen" by the photoconductive cell which has a peak response to the light of this wavelength. The electrical signal produced by the photoconductive cell is proportional to the amount of light striking it which, in turn, is proportional to the amount of ultraviolet light striking the phosphor. The electrical signal from the photoconductive cell is passed to control circuit 57 which actuates an electrically operated shut-off valve 59 when the ultraviolet radiation drops below a set level.

End members 19 and 21 provide closures at either end of tubular member 1. End member 19 has an inlet port 23 which leads into an inlet annular chamber 25. Chamber 25 is connected to annular passageway 15 by an inlet metering annulus 27. Passageway 15 is connected to outlet port 29 in end member 21 through an outlet annulus 31 and outlet annular chamber 33.

A pair of annular rings 35 and 37 are mounted around quartz cylinder 3 at either end thereof. Extending between rings 35 and 37 are three post members 39, 40 and 41 forming a wiper cage and having attached thereto three stainless steel wiper blades 42, 43 and 44 which contact and ride on the surface of quartz cylinder 3. Ring 37 is attached to ring gear 45 which is driven by spur gear 47 mounted on shaft 49. Shaft 49 in turn is driven by motor 51.

The ultraviolet sensor 55 is provided with sensor wipers 61, 63, 65 which serve to keep the surface of the sensor free of foreign deposits from the water which might settle on the surface. The wipers consist of three 0.005 thick blades of stainless steel attached to the wiper cage and which pass by the sensor as the wiper cage is continuously rotated by an electric motor 51. These blades are perforated with a series of holes to allow the ultraviolet light to reach the sensor as the wiper passes by.

A flow-sensing switch 71 is located at the outlet of the unit and switches to the "ON" state whenever water is flowing through the unit and remains in the "OFF" state when no flow occurs. This switch 71 is connected to a control circuit 73 which increases the output of the ultraviolet generators when flow occurs, thus providing intense radiation which effectively kills the microorganisms in the water. When no flow occurs, the control circuit 73 reduces the output of the ultraviolet generators to a level which just maintains the arc in the lamps and keeps the lamps "warm" and ready to provide maximum ultraviolet output when the flow begins again.

In normal domestic use, the "no flow" condition occurs for much longer periods than the "flow" condition; therefore, the lamp envelope is exposed to the lower level of ultraviolet radiation most of the time. This reduces the solarization effect and greatly extends the useful life of the lamps. In addition to increasing the life of the lamps, the decreased ultraviolet output during no flow periods serves to conserve energy as the power consumed by the lamps during this period is about 10% of the power used during the periods of water flow.

In operation the unit is installed in existing lines. Water enters inlet port 23 and flows into passageway 15 through inlet metering annulus which is designed to limit the flow to remain within the treatment capacity of the unit. As the water flows through passageway 15 formed between tubular member 1 and quartz cylinder 3, the ultraviolet tubes 5-8 emit radiation which kills all germs and microorganisms present in the water.

Cylinder 3 is constructed of quartz because of its property of efficiently transmitting ultraviolet radiation. The optical properties of the quartz cylinder 3 must be protected from deterioration which could result from the depositing of sediment and minerals contained in the water. Motor 51 drives the annular ring assembly carrying stainless steel wiper blades 42-44 and these wiper blades ride over and wipe clean the surface of quartz cylinder 3 to prevent any decrease in usuable ultraviolet radiation.

What is claimed is:

1. A water purification system utilizing ultraviolet radiation comprising
    an elongated outer enclosure having an inlet and an outlet for the passage of water,
    a transparent cylindrical enclosure mounted coextensively within said outer enclosure to define a passageway for water therebetween,
    ultraviolet radiation means mounted within said transparent cylindrical enclosure,
    first and second annular members mounted for rotation at opposite ends of said transparent cylindrical enclosure,
    a plurality of metallic wiper blades extending parallel to the longitudinal axes of said cylindrical enclosures and connected between said first and second annular members within said passageway in position to have an edge portion in wiping contact with the outer surface of said transparent cylindrical enclosure, and
    means to operate said wiper blades around said transparent enclosure to continually remove sediment and impurities deposited on the surface by the water passing through said passageway, said means to operate said wiper blades comprising a drive motor coupled to one of said annular members,
    whereby the efficiency of optical transmission of the ultraviolet radiation through said transparent enclosure will be maintained at an optimum value.

2. The combination according to claim 1 wherein
    said passageway has constricted portions at the inlet and outlet to conrol the flow of water to remain within the maximum rate of treatment allowable with the particular ultraviolet radiation means utilized.

3. The combination according to claim 1 comprising
    a monitoring peep-hole located in said outer enclosure to permit view of the interior operation.

4. The combination according to claim 1 comprising
    an ultraviolet sensor mouned on said outer enclosure and exposed to ultraviolet radiation within said passageway, and
    first control circuit means connected to said ultraviolet sensor and operated thereby in response to the electrical signal generated by said ultraviolet sensor.

5. The combination according to claim 4 comprising
    an electrically operated shut-off valve positioned in the inlet of said system and connected to said first control circuit means to shut-off the flow of water when said ultraviolet sensor indicates a predetermined drop in the radiation level.

6. The combination according to claim 4 comprising
    a plurality of perforated wiper blades mounted for circular movement within said outer enclosure in position to remove foreign deposits from said ultraviolet sensor.

7. The combination according to claim 1 comprising
    a flow-sensing switch positioned in the outlet of said system,
    second control circuit means connected to said flow-sensing switch and operated thereby to control the radiation output of said ultraviolet radiation means.

* * * * *